United States Patent [19]

Van Iten

[11] Patent Number: 5,558,662
[45] Date of Patent: Sep. 24, 1996

[54] ABSORBENT ARTICLE HAVING AN ATTACHMENT MECHANISM AND A METHOD OF ATTACHING

[75] Inventor: Thomas P. Van Iten, Neenah, Wis.

[73] Assignee: Kimberly-Clark Corporation, Neenah, Wis.

[21] Appl. No.: 230,563

[22] Filed: Apr. 20, 1994

[51] Int. Cl.$^6$ .................................................. A61F 13/15
[52] U.S. Cl. ..................... 604/387; 604/385.1; 604/386
[58] Field of Search .................... 604/385.1–402

[56] References Cited

U.S. PATENT DOCUMENTS

| | | | |
|---|---|---|---|
| 2,787,271 | 4/1957 | Clark | 128/290 |
| 3,111,737 | 11/1963 | Heil | 24/201 |
| 3,161,932 | 12/1964 | Russell | 24/203 |
| 3,372,443 | 3/1968 | Daddona, Jr. | 24/201 |
| 3,888,255 | 6/1975 | Shah et al. | 128/290 R |
| 3,919,743 | 11/1975 | Cutler | 24/201 B |
| 4,249,267 | 2/1981 | Voss | 2/69 |
| 4,399,591 | 8/1983 | Yoon et al. | 24/201 B |
| 4,589,876 | 5/1986 | Van Tilburg | 604/385 R |
| 4,608,047 | 8/1986 | Mattingly | 604/387 |
| 4,710,979 | 12/1987 | Bull et al. | 2/48 |
| 4,746,494 | 4/1988 | Marchesi | 24/303 |
| 4,779,314 | 10/1988 | Aoki | 24/303 |
| 4,882,815 | 11/1989 | Nilsen | 24/303 |
| 4,900,320 | 2/1990 | McCoy | 604/387 |
| 4,917,697 | 4/1990 | Osborn, III et al. | 604/387 |
| 5,098,422 | 3/1992 | Davis et al. | 604/385.1 |
| 5,103,501 | 4/1992 | Meisels . | |
| 5,217,448 | 6/1993 | Glaug et al. | 604/397 |
| 5,221,275 | 6/1993 | Van Iten | 604/387 |
| 5,300,058 | 4/1994 | Buell | 604/385.2 |
| 5,300,461 | 7/1994 | Leeker | 604/387 |

FOREIGN PATENT DOCUMENTS

| | | |
|---|---|---|
| 0446818A2 | 9/1991 | European Pat. Off. . |
| 0511905 | 11/1992 | European Pat. Off. ............... 604/387 |
| 2492238 | 10/1980 | France . |
| 3736254A1 | 5/1989 | Germany . |
| 48-73497 | 9/1973 | Japan . |
| 586322 | 11/1993 | Japan . |
| 2045335 | 10/1980 | United Kingdom . |

OTHER PUBLICATIONS

Japanese Publication No. 46–12554.
Japanese Publication No. 40–36391.
Nippon Bascon KK—The Second Skin —A New Napkin: Knight Star Code: 857–8499.

Primary Examiner—John G. Weiss
Assistant Examiner—K. M. Reichle
Attorney, Agent, or Firm—Thomas J. Connelly

[57] ABSTRACT

An absorbent article having an attachment mechanism is disclosed along with a method of attaching the absorbent article to an undergarment. The absorbent article includes an absorbent and a baffle secured to the absorbent. The baffle has first and second longitudinal side edges, a first end, and first and second appendages extending laterally outward from the first and second longitudinal side edges, respectively. Each of the first and second appendages are positioned adjacent to the first end and aligned at an angle relative to the longitudinal side edges. Each appendage has a sufficient length to be folded inward and overlap the other appendage. The absorbent article further includes a first magnet positioned on or secured to the baffle and a second magnet secured to one of the appendages. The method includes positioning the absorbent article on an undergarment with the baffle contacting an interior surface of the undergarment. The appendages are then folded around the undergarment such that the appendage containing the second magnet overlays the other appendage. The second magnet is brought into alignment with the first magnet to hold the absorbent article secure to the undergarment.

2 Claims, 5 Drawing Sheets

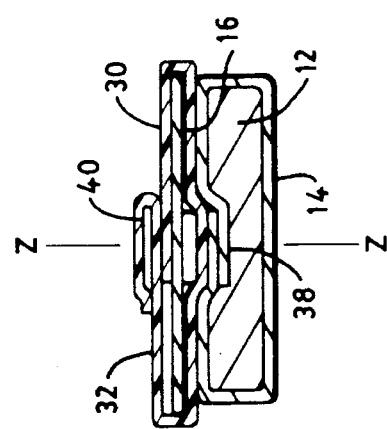
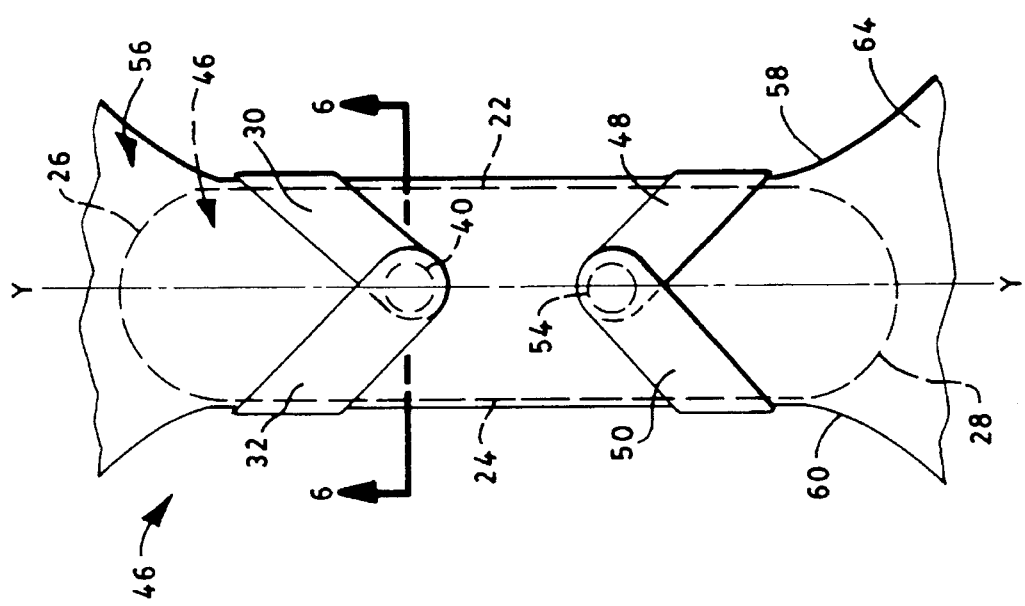

ABSORBENT ARTICLE HAVING AN ATTACHMENT MECHANISM AND A METHOD OF ATTACHING

FIELD OF THE INVENTION

This invention relates to an absorbent article having an attachment mechanism and a method of attaching the absorbent article to a crotch portion of an undergarment. More particularly, this invention relates to a sanitary napkin having a magnetic attachment mechanism.

BACKGROUND OF THE INVENTION

The most common known and used fastener for absorbent articles such as sanitary napkins, panty liners, diapers, incontinence garments, training pants, shields, etc. is adhesive. Adhesives, especially garment-attachment adhesives which are designed to directly adhere to an undergarment, exhibit some problems. First, they have a tendency to leave a residue on the undergarment and after a number of applications, this build up can result in undesirable tactile properties and/or discoloration. Such discoloration may cause the user to eventually discard the undergarment before it would normally be discarded. Second, the adhesive can stick to the skin and cause discomfort. Third, even though adhesives are relatively inexpensive, a peel strip is required to be placed over the adhesive, prior to use, to protect it from becoming contaminated. The cost of the peel strip along with the extra cost of cutting, aligning and placing the peel strip over the adhesive increases the total cost of manufacturing the product.

"VELCRO" and other types of hook and loop fasteners are just making their entry into the marketplace. While some attention has been given to magnetic catches and closures for uses with clothing, there has been little use or attention given to such means for catamenial devices. Generally speaking, this has probably been due to the fact that garment-attachment adhesives are relatively inexpensive and lend themselves well to a manufacturing process where they can be sprayed or coated onto a moving web at fast speeds. Also, there have been problems maintaining magnetic strength with inexpensive materials, the weight and bulk of the closure for the desired strength, and their relative inflexibility. Consequently, magnetic fasteners are not currently utilized on hygienic absorbent articles.

However, there remains a real need for an absorbent article, like a sanitary napkin, having some type of simple and inexpensive fastener for holding the article secure to the crotch portion of an undergarment. There is also a need for a fastener which can be readily and easily opened and/or refastened a plurality of times without loosing it's strength. Furthermore, there is a need for an absorbent article having a fastener which will not damage the undergarment to which it is attached.

Now an absorbent article having a unique attachment mechanism has been invented along with a method of attaching the absorbent article to a crotch portion of an undergarment.

SUMMARY OF THE INVENTION

Briefly, this invention relates to an absorbent article having an improved attachment mechanism and a method of attaching the absorbent article to a crotch portion of an undergarment. The absorbent article includes an absorbent and a baffle secured to the absorbent. The baffle has first and second longitudinal edges, a first end, and first and second appendages extending laterally outward from the first and second longitudinal edges. Each of the first and second appendages are aligned at an angle relative to the first end and each has a sufficient length to be folded inward and overlap one another. The article further includes a first attachment member secured to the baffle and a second attachment member secured to the first appendage. The first and second attachment members can be magnets which are attracted to one another once they are superimposed.

The method includes positioning the absorbent article on an undergarment with the baffle contacting an interior surface of the undergarment. The appendages are then folded around the edges of the undergarment such that the first appendage overlays the second appendage. The magnet in the first appendage is then brought into alignment with the magnet secured to the baffle to hold the absorbent article secure to the undergarment.

The general object of this invention is to provide an absorbent article having an improved attachment mechanism and a method of attaching the absorbent article to a crotch portion of an undergarment. A more specific object of this invention is to provide a sanitary napkin having a magnetic attachment mechanism.

Another object of this invention is to provide an absorbent article with an attachment mechanism which, unlike a garment adhesive, does not damage the undergarment.

A further object of this invention is to provide an absorbent article with an attachment mechanism which can be fastened and unfastened numerous times without minimizing the strength of the attachment mechanism.

Still another object of this invention is to provide an absorbent article with an inexpensive attachment mechanism.

Still further, an object of this invention is to provide an absorbent article with an attachment mechanism which is easy to fasten.

Still further, an object of this invention is to provide an absorbent article with an attachment mechanism which is relatively easy to incorporate into a manufacturing process.

Other objects and advantages of the present invention will become more apparent to those skilled in the art in view of the following description and the accompanying drawings.

BRIEF DESCRIPTION OF THE DRAWINGS

FIG. 5 is a bottom view of the absorbent article depicted in FIG. 3 attached to the crotch portion of an undergarment.

FIG. 6 is a cross-sectional view of the absorbent article depicted in FIG. 5 taken along line 6—6 showing the alignment of the magnets.

DETAILED DESCRIPTION OF THE PREFERRED EMBODIMENTS

Figure 1:
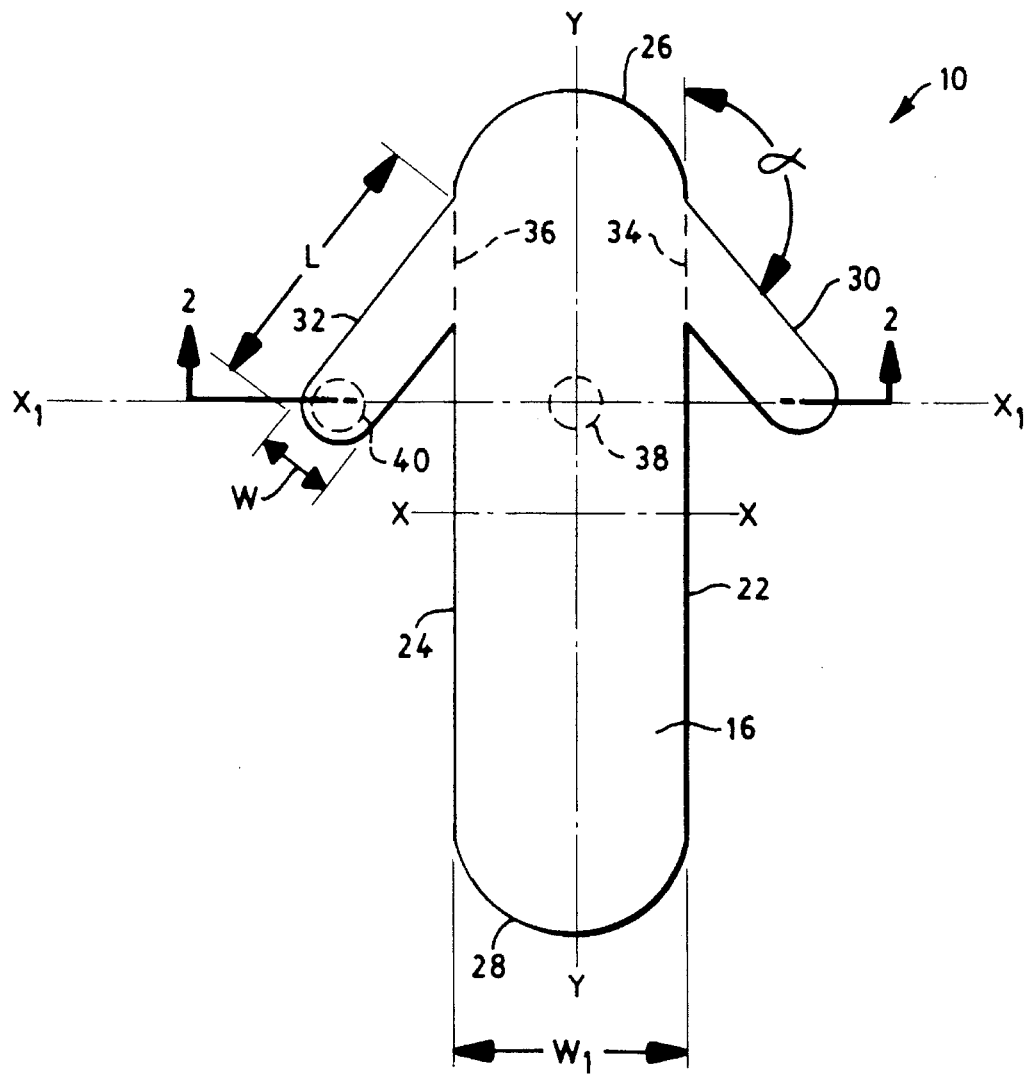
FIG. 1 is a bottom view of an absorbent article having an attachment mechanism including a pair of laterally extending appendages and first and second magnets, one of the magnets being secured to the absorbent body and the other magnet being secured to one of the appendages.
Figure 2:
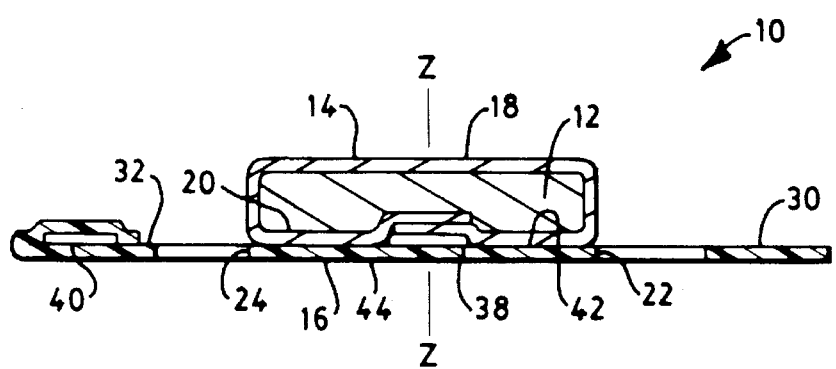
FIG. 2 is a cross-sectional view of the absorbent article shown in FIG. 1 taken along line 2—2.

Referring to FIGS. 1 and 2, an absorbent article 10 is shown having an absorbent 12 wrapped by a cover 14 and secured to a baffle 16. The absorbent article 10 is shown in the form of a sanitary napkin having a multi-layered construction. Although the absorbent article 10 is depicted as a sanitary napkin, it could also be a panty liner, a disposable diaper, an incontinence garment, a training pant, a shield, etc.

The absorbent 12 has a body-facing surface 18 and a garment-facing surface 20. The body first facing surface 18 is designed to be positioned adjacent to the torso of a body when the absorbent article 10 is worn and the garment-facing surface 20 is designed to be positioned adjacent an interior surface of the crotch portion of arm undergarment.

The absorbent 12 can be made from natural or synthetic fibers. Natural fibers include cellulose fibers such as wood pulp, cotton or regenerated cellulose. Synthetic fibers can include polyesters or polyolefins with polyethylene or polypropylene fibers being preferred. The absorbent 12 could also be constructed from coform, which is a blend of pulp and synthetic meltblown fibers. A preferred absorbent material for use in a sanitary napkin is a combination of wood pulp and coform. When synthetic fibers are used, the fibers can be treated with a surfactant to it's wettability.

The absorbent 12 can also contain a hydrocolloidal material, commonly referred to as a superabsorbent. Superabsorbents are normally added to the absorbent 12 to increase the amount of fluid which the absorbent 12 can contain and also to increase fluid retention capabilities. The superabsorbent can be added as individual particles or it can be formed as a laminate structure having a superabsorbent material incorporated onto a carrier sheet.

The cover 14 can be constructed of a natural or a synthetic material and should be easily penetrated by body fluids such as menstrual fluid, blood, urine, etc. Suitable materials include those materials that have a soft hand, such as polyolefin spunbond, which is manufactured and sold by Kimberly-Clark Corporation. The cover could also be made out of a bonded carded web of polyester, polypropylene, polyethylene, nylons, or other similar type fibers. Other polyolefins, such as linear low density polypropylene, linear low density polyethylene, finely-perforated film webs and net materials can also be used. If a thermoplastic film is used, it may be necessary to perforate or slit the film so as to make it liquid permeable.

In FIG. 2, the cover 14 is shown wrapping completely about the absorbent 12. However, it is possible for the cover 14 to cooperate with the baffle 16 to enclose the absorbent 12. Various methods of securing the cover 14 to the baffle 16 are known to those skilled in the art.

The baffle 16 can be liquid-impermeable which will permit the passage of air and moisture vapor out of the absorbent 12 while blocking the passage of fluids or liquids therefrom. The baffle 16 could also be an air permeable micro-porous film which would prevent liquids from passing therethrough. The baffle 16 can be a foam, for example, a polyolefin foam or a polyurethane foam. A polyolefin foam can be made from polyethylene or polypropylene. The baffle 16 can be constructed of a liquid-permeable foam that has been treated or coated to make it liquid impermeable. For purposes of this invention, the baffle 16 is preferably a closed cell polyolefin foam having as thickness in the range of about 0.2 mm to about 2.0 mm, preferably about 0.4 mm to about 1.6 mm, and more preferably, about 0.04 mm to about 0.8 mm. Closed cell foams tend to work best. Such a foam is sold under the trademark "VOLARA" and is distributed by Voltex, a division of Sekisui America Corporation, having an address at 100 Shepard Street, Lawrence, Mass. 01843. A closed cell foam having a thickness as specified above, has sufficient strength which allows it to be folded over upon itself without ripping or tearing.

The baffle 16 can be secured to the absorbent 12 by a construction adhesive (not shown) and/or it can attached to the cover 14. It should be noted that the baffle 16 can be attached directly to the absorbent 12 and/or the cover 14 by means other than adhesive. For example, the attachment can be accomplished by the use of heat and/or pressure, ultrasonic bonding, mechanical fasteners, etc.

Referring again to FIG. 1, the baffle 16 has first and second longitudinal side edges 22 and 24 which can be arranged so as to coincide with the longitudinal side edges of the absorbent 12 and/or the longitudinal side edges of the cover 14. Likewise, the longitudinal side edges 22 and 24 can be spaced inward or outward from the side edges of the absorbent 12. Preferably, the longitudinal side edges 22 and 24 will approximately coincide with the longitudinal side edges of the absorbent 12. The longitudinal side edges 22 and 24 can be linear or nonlinear and they can be aligned parallel or at an angle relative to one another. In FIG. 1, the longitudinal side edges 22 and 24 are linear and are aligned parallel to one another. The baffle 16 also contains a first end 26 and a second end 28. The first end 26 is spaced apart from and oppositely aligned with the second end 28.

The baffle 16 further contains first and second appendages 30 and 32 which extend laterally outward from the longitudinal side edges 22 and 24, respectively. The appendages 30 and 32 are integrally formed with the baffle 16 and have approximately the same thickness as the main portion of the baffle 16. The appendages 30 and 32 are shown as finger-like or ribbon-like members having a length L and a width W. When the absorbent article 10 is a sanitary napkin having an absorbent 12 with a width $W_1$ of about 2 to about 4 inches (about 51 mm to about 102 mm), the length of the appendages 30 and 32 should be such that they span across more than half of the width $W_1$ and are capable of overlapping one another. In other words, when the appendages 30 and 32 are folded adjacent to the longitudinal edges 20 and 24, they should overlap one another and cross the longitudinal central axis Y—Y.

Figure 7:
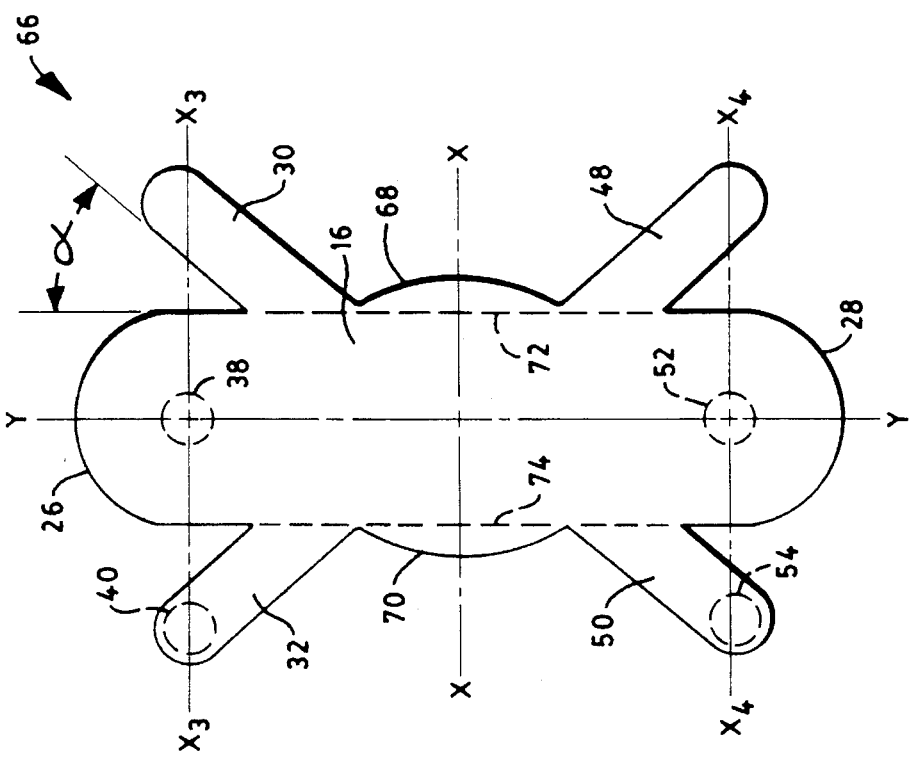
FIG. 7 is a bottom view of an alternative embodiment of an absorbent article having an attachment mechanism including two pairs of laterally extending appendages which are aligned at an acute angle relative to the longitudinal side edges of the absorbent article.

The width W of the appendages 30 and 32 can vary from between about 0.25 inches (about 6.35 mm) up to a width which would be approximately equal to the length of the absorbent article 10. More preferably, the width W of the appendages 30 and 32 will vary between about 0.25 inches to about 1.0 inches (about 6.35 mm and about 25.4 mm), and most preferably, between about 0.5 inches to about 0.75 inches (about 0.72 mm to about 19.0 mm). Each of the appendages 30 and 32 are aligned at an angle alpha ($\alpha$) adjacent to the first end 26 and relative to the first and second longitudinal side edges, 22 and 24 respectively. The angle alpha ($\alpha$) can be an acute angle (less than 90 degrees) as shown in FIG. 7 or it can be an obtuse angle (greater than 90 degrees and less than 180 degrees) as is depicted in FIG. 1. When the appendages 30 and 32 are aligned at an acute angle, the angle ($\alpha$) should preferably be less than 60 degrees, and most preferably, should be between about 10 to 50 degrees. When the appendages 30 and 32 are aligned at an obtuse angle, the angle alpha ($\alpha$) should preferably be greater than about 100 degrees, and most preferably, should be between about 110 and 170 degrees.

It has been found that when the appendages 30 and 32 are aligned at either an acute or an obtuse angle relative to longitudinal side edges 22 and 24, they can be folded around the crotch portion of an undergarment very easily. In the folded position, the appendages 30 and 32 will prevent longitudinal movement of the absorbent article 10 relative to the undergarment itself. If the appendages 30 and 32 are aligned perpendicular (at 90 degrees) relative to the longitudinal side edges, 22 and 24 respectively, they will not be as successful in preventing longitudinal movement relative to the undergarment. The perpendicular alignment does prevent sideways or transverse movement of the absorbent article 10 relative to the undergarment and can be used if desired.

Referring again to FIG. 1, the appendages 30 and 32 are a mirror image of one another when the absorbent article 10 is divided along the longitudinal central axis Y—Y. It should be noted that the appendages 30 and 32 are shown as having the same length L and width W, although it is possible to make one longer or wider than the other if desired. The two appendages 30 and 32 are designed to be folded along fold lines 34 and 36, respectively, so that they can wrap around the outside edge of the undergarment and overlap the width of the crotch portion. The fold lines 34 and 36 can be imaginary lines on which the appendages 30 and 32 are folded or they can be actual hinges formed in a predetermined location on which the appendages 30 and 32 have to fold.

The absorbent article 10 further includes attachment means for securely holding the absorbent article 10 to the crotch portion of an undergarment. The attachment means consist of a first member 38 and a second member 40. The first member 38 is secured to one of the surfaces of the baffle 16. In FIG. 2, the first member 38 is positioned between the absorbent 12 and the baffle 16. The first member 38 is preferably aligned close to or in alignment with the longitudinal central axis Y—Y. The first member 38 is offset from the transverse central axis X—X of the absorbent article 10 although it could also be aligned therewith if desired. By offsetting the first member 38 from the transverse central axis X—X, one decreases the possibility that the wearer could feel the present of it.

The first and second members, 38 and 40 respectively, can be magnets or some other type of device which can exert an attractive force when superimposed and aligned close to one another. The magnets provide an easy way for the user to reposition the absorbent article 10 relative to the undergarment should the need arise. One of the first and second members, 38 and 40 respectively, can consist of a permanent magnet and the other member can be a receiver member having a magnetically susceptible metal engageable with the permanent magnet. The first member 38 can be a fixed magnetic element while the second attachment member 40 can be a moveable magnetic element or vice versa.

When the first and second members, 38 and 40 respectively, are magnets and/or receiver members, they should be wafer thin so the wearer of the absorbent article 10 will not notice them. The magnets and/or receiver members should have a thickness of less than about 0.25 inches (about 6.35 mm) and preferably less than about 0.12 inches (about 3.2 mm). A thickness of less than about 0.10 inches (about 2.54 mm) is most preferred. The magnets can be constructed of a neodymium-iron-boron material, a ceramic material or any other type of material having a ferrite base. The magnets and receiver members should have a holding force, when measured perpendicular to one another, of less than about 2.0 pounds, preferably less than about 1.0 pound, and most preferably, less than about 0.75 pounds. If the strength of the magnets and/or receiver members is too strong, it may be difficult for a person using the absorbent article 10 to separate the attachment. If the strength of the magnets and/or receiver members is too weak, the attachment may not be adequate to secure the absorbent article 10 to the crotch portion of an undergarment.

The first member 38 can be secured to either a body-facing surface 42 or a garment-facing surface 44 of the baffle 16. The first member 38 can be secured by an adhesive or by embedding the first member 38 into the foam baffle 16. When the first magnet 38 is positioned on the body-facing surface 42 of the baffle 16, the magnetic force of the first magnet 38 to the second magnet 40 may cause the first magnet 38 to be implanted into the polyolefin foam. If this occurs, it may not be necessary to secure the first magnet 38 to the foam by an adhesive. Likewise, the first magnet 38 can be merely positioned on the body-facing surface 42 of the baffle 16 and be held in place by direct contact with either the absorbent 12 or the cover 14. It is also possible for the first member 38 to be secured to either the cover 14 or the absorbent 12 by an adhesive or by another type of bonding agent. It is further possible to embed the first member 38 in the absorbent 12 or to position it between the cover 14 and the baffle 16 and to hold it there by the bond which secures the absorbent 12 to the baffle 16.

The second member 40 can be secured near the free end of either the first or second appendages, 30 or 32 respectively. In FIG. 2, the second member 40 is shown secured to the second appendage 32. The second appendage 32 can have it's free or distal end folded over to enclose the second member 40 therebetween. It should be noted that the length of the appendage 30 or 32, which has the second member 40 enclosed or secured thereto, should be approximately the same length as the other appendage 30 or 32. As with the first member 38, the second member 40 can be secured by an adhesive, be bonded in place by heat or pressure, or be secured by a mechanical means such as by sewing, stapling, etc.

In FIG. 2, the second member 40 is depicted as a wafer thin magnet, in the form of a circular disk. The magnet is positioned on the body-facing surface 42 of the baffle 16 and has the free end of the second appendage 32 folded over it. The baffle 16 also has a garment-facing surface facing 44 and it is possible for the second member 40 to be placed adjacent to the garment-facing surface 44 and then have the free end of the second appendage 32 wrapped under it.

Referring again to FIG. 1, the absorbent article 10 is shown having a central transverse axis X—X and the first and second members, 313 and 40 respectively, are shown aligned along a transverse axis $X_1$—$X_1$ which is spaced apart from the transverse central axis X—X. This configuration places the first and second appendages, 30 and 32 respectively, closer to the first end 26. It has been found that by placing the appendages 30 and 32 closer to an end of the absorbent article 10, that the first and second members 38 and 40 respectively, can be located away from the central transverse axis X—X of the article 10 which is the area which is wetted by body fluids. By placing the first and second members 38 and 40 closer to one of the ends, it has been found that the user will not notice the weight of the magnets as much as if they were in the center portion of the absorbent article 10.

When the second member 40 is secured to the second appendage 32 and the second appendage 32 is folded on the fold line 36, it should vertically overlap the first member 38. This can be obtained when the first member 38 is situated at the intersection of the longitudinal axis Y—Y and the transverse axis $X_1$—$X_1$ and the second member 40 is secured to the second appendage 32 and located along the transverse axis $X_1$—$X_1$. It should be noted that the first and second members, 38 and 40 respectively, can be offset from the transverse axis $X_1$—$X_1$ but the size and shape of the first and second members, 38 and 40 respectively, may have to be enlarged. Such an offset will also depend on the angle at which the appendage 32 is folded and the orientation of the fold line 36 relative to the longitudinal side edge 24. However, when the first and second members, 38 and 40 respectively, are each in the form of a thin magnetic disk, having a diameter of about 0.5 to 1.0 inches (about 12.7 mm to 25.4 mm) or less, it is beneficial to arrange the first and second members 38 and 40 such that they will substantially overlap one another when the appendages 30 and 32 are folded. This will assure that adequate magnetic strength is present to provide a secure attachment.

It should be noted that the magnets can vary in configuration and include circular disks, squares, rectangles or any other geometric shape. For manufacturing purposes, a circular disk works fine.

Figure 3:
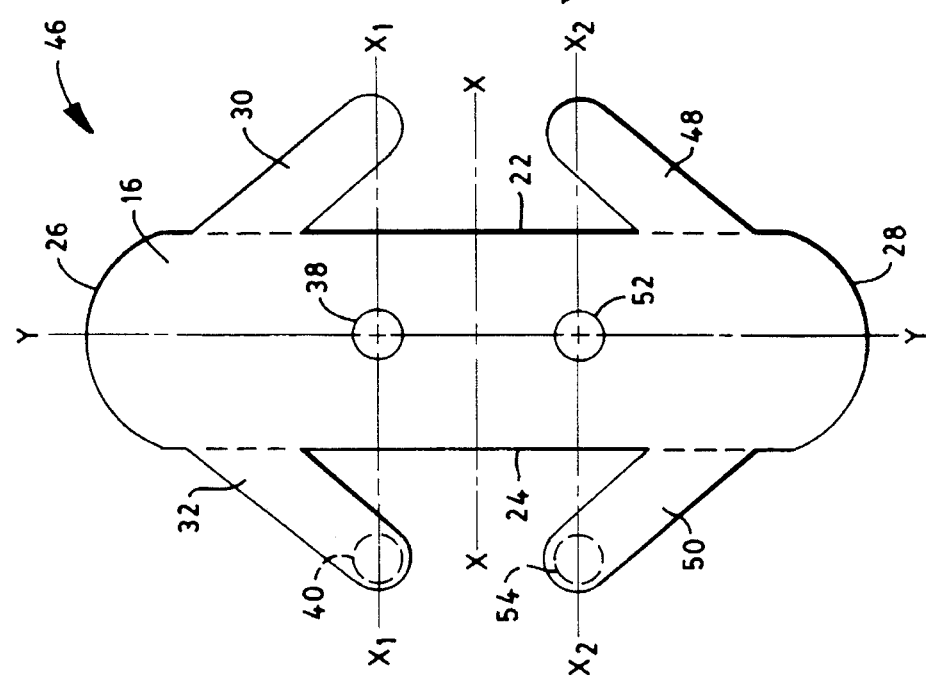
FIG. 3 is a bottom view of an alternative embodiment of an absorbent article having an attachment mechanism including two pairs of laterally extending appendages and two sets of magnets, a first magnet of each set being positioned on the absorbent body and the second magnet of each set being secured to one appendage from each pair.

Referring to FIG. 3, an absorbent article 46 is shown which is similar to that shown in FIG. 1, except for a couple of differences. First, it has a second pair of appendages 48 and 50 which are formed at an obtuse angle relative to the second end 28. If the absorbent article 46 was folded on the central transverse axis X—X, the upper half would be a mirror image of the lower half. Second, the absorbent article 46 contains third and fourth attachment members, 52 and 54 respectively. The third attachment member 52 can be a magnet located at the intersection of the longitudinal axis Y—Y and the transverse axis $X_2$—$X_2$. The transverse axis $X_2$—$X_2$ is spaced apart from the central transverse axis X—X. The third member 52 can be similar in all respects to the first member 38. Third, the first and third attachment members 38 and 52 are secured to the garment-facing surface 44 of the baffle 16. Fourth, the fourth attachment member 54 is secured to the appendage 50 in a similar fashion as was the second member 40 is secured to the appendage 32. It should be noted that the first and second sets of attachment members 38 and 40, and 52 and 54 respectively, can be identical or can differ depending upon the desires of the manufacturers.

Figure 4:
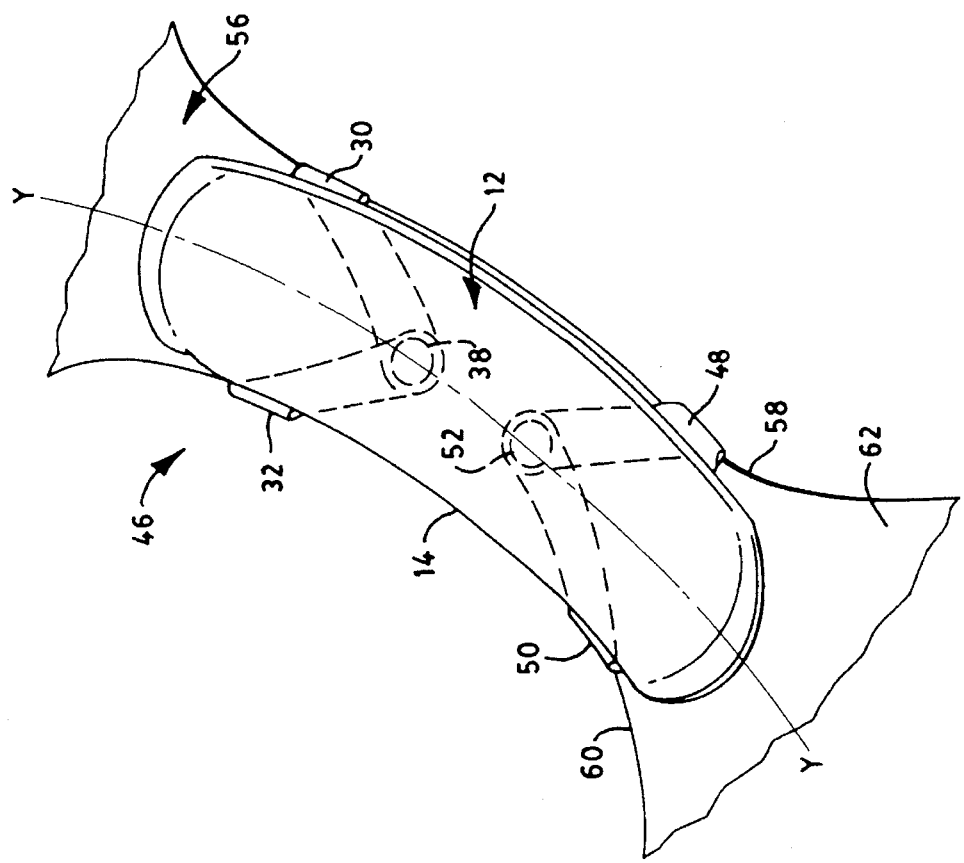
FIG. 4 is a perspective view of the absorbent article depicted in FIG. 3 attached to the crotch portion of an undergarment.

Referring to FIG. 4, the absorbent article 46 is shown secured to a crotch portion of an undergarment 56. The undergarment 56 contains two longitudinal side edges 58 and 60 which will be covered by the absorbent article 46. The longitudinal side edges 58 and 60 can coincide with the longitudinal side edges of the baffle, 22 and 24 respectively, or they can be slightly inward thereof. The undergarment 56 also contains an interior surface 62 which contacts the garment-facing surface 44 of the baffle 16.

Referring to FIG. 5, the undergarment 56 is shown having an exterior surface 64 around which is wrapped the first and second sets of attachment members 30 and 32, and 48 and 50. The appendages 30 and 32 are folded around the crotch portion of the undergarment 56 and overlap such that the magnets 38 and 40 will be approximately vertically aligned. In this position, the first appendage 30 (the one without the magnet 40) is first folded over the magnet 38 and then the second appendage 32 (containing the magnet 40) is folded over the first appendage 30. The first and second appendages, 30 and 32 respectively, overlay the first magnet 38 and the magnetic force of the magnets 38 and 40 will hold the absorbent article 46 secure to the undergarment 56. Likewise, the third and fourth appendages, 48 and 50 respectively, are folded in a similar fashion such that the third appendage 48 is first folded against the exterior surface 64 of the undergarment 56 and then the fourth appendage 50 is folded over it. The magnet 52 is attracted to the magnet 54 and provides a secure attachment between the absorbent article 46 and the undergarment 56.

Referring to FIG. 6, the position of the folded appendages 30 and 32 are shown wherein the first and second magnets, 38 and 40 respectively, are vertically aligned or superimposed relative to one another along the central Z—Z axis.

Figure 8:
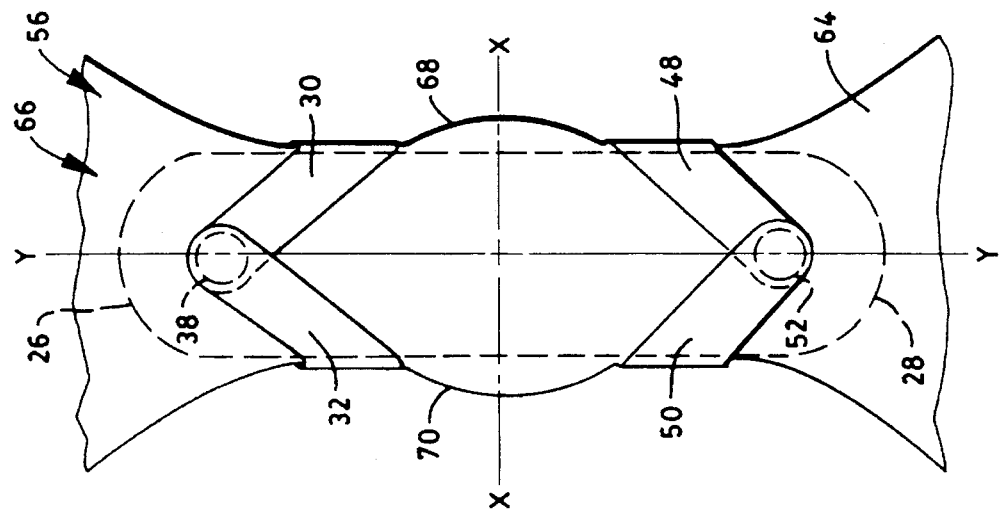
FIG. 8 is a bottom view of the absorbent article depicted in FIG. 7 attached to the crotch portion of an undergarment.

Referring to FIGS. 7 and 8, an absorbent article 66 is shown which is similar to that shown in FIG. 3 except for a few differences. The first difference is that the magnets 38 and 52 are secured to the body-facing surface 42 of the baffle 16. A second difference is that the first pair of appendages 30 and 32 are aligned adjacent to the first end 26 at an acute angle alpha ($\alpha$) and the second pair of appendages 48 and 50 are aligned adjacent to the second end 28 at an acute angle alpha ($\alpha$). The first pair of appendages 30 and 32 are formed along a transverse axis $X_3$—$X_3$ and the second pair of appendages 48 and 50 are formed along a transverse axis $X_4$—$X_4$. Both of these axes are spaced apart from the central transverse axis X—X. When the appendages 30 and 32, and 48 and 50 are folded under and around the exterior surface 64 of the undergarment 56, they will be attached as is shown in FIG. 8. The appendages 30 and 32 will angle toward the first end 26 while the appendages 48 and 50 will angle toward the second end 28. This configuration places the magnets farther away from the center of the absorbent article 66 so that they are less noticeable by the wearer. The angular disposition of the appendages 30 and 32, and 48 and 50 prevent the absorbent article 66 from moving longitudinally along the Y—Y axis with respect to the undergarment 56. When two pairs of appendages 30 and 32, and 48 and 50 are present, the absorbent article 66 is more stable in that forward and backward sliding relative to the undergarment 56 is diminished. The acute or obtuse angle of the appendages 30 and 32, and 48 and 50 play a significant role in preventing longitudinal movement of the absorbent article 66 with respect to the undergarment 56.

A third difference exhibited in FIGS. 7 and 8 is that the absorbent article 66 has nonlinear longitudinal side edges 68 and 70 located between the outward extending pairs of appendages 30 and 32, and 48 and 50 respectively. The nonlinear side edges 68 and 70 are convex, such that they extend laterally outward. The amount that the edges 68 and 70 extend outward can vary depending upon one's needs. The outwardly extending longitudinal side edges 68 and 70 are formed from the baffle 16 alone and are capable of folding along longitudinal axes, 72 and 74 respectively, as they contact the inner thighs of a woman who is wearing the absorbent article 66. The side edges 68 and 70 serve as fluid barriers to protect the undergarment 56 from becoming stained should any body fluid flow off the top surface of the absorbent article 66.

Figure 9:
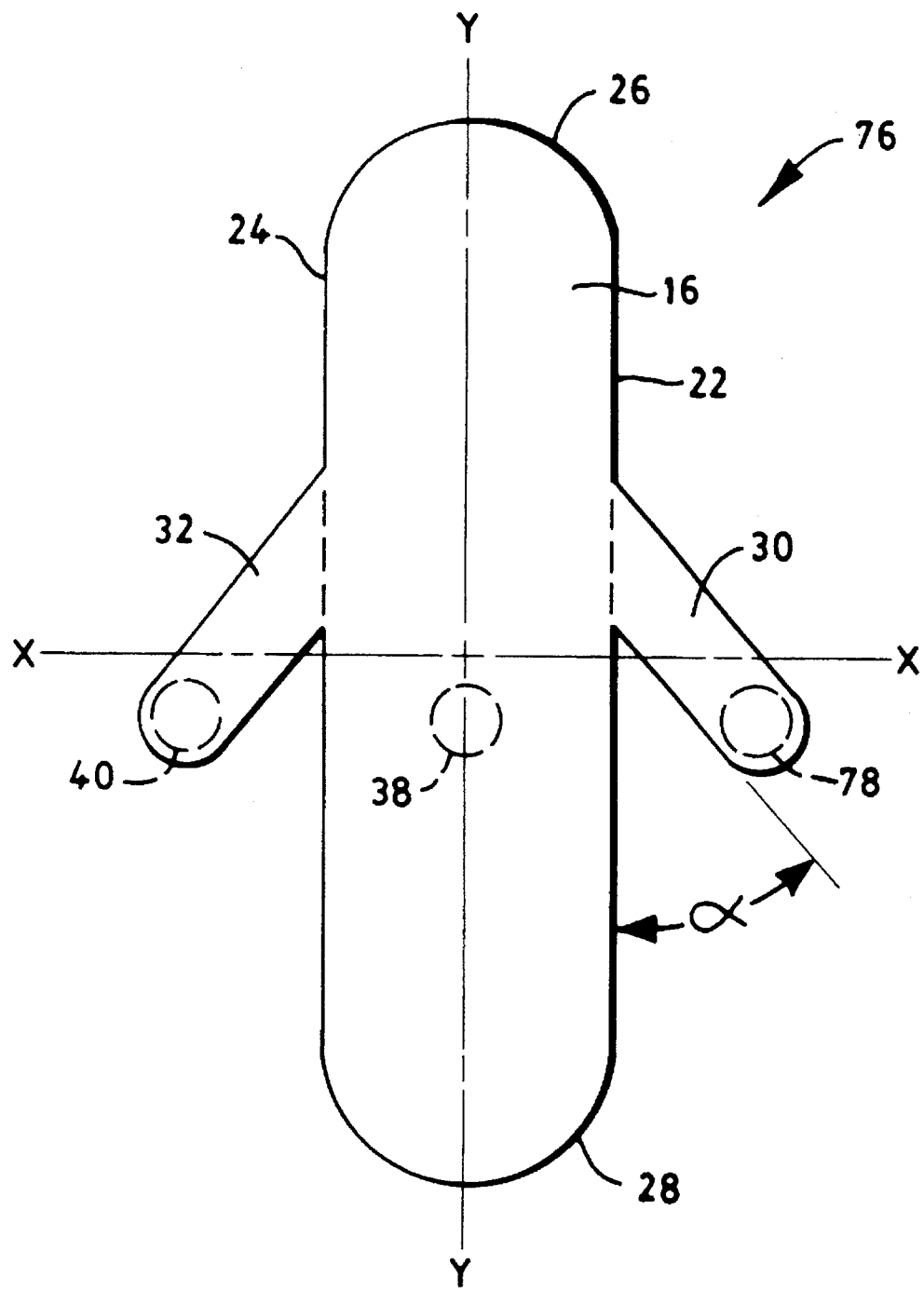
FIG. 9 is a bottom view of an alternative embodiment of an absorbent article having an attachment mechanism including a pair of laterally extending appendages and three magnets, one of the magnets being positioned on the absorbent body and the other two magnets being secured to each of the appendages.

Referring to FIG. 9, an absorbent article 76 is shown which is similar to that shown in FIG. 1, except for two differences. The first difference is that the midpoint of each appendage 30 and 32 intersects the longitudinal side edges 22 and 24 at a location which is equal distance from the first and second ends, 26 and 28 respectively, (along the central transverse axis X—X). The first and second appendages, 30 and 32 respectively, are aligned at an acute angle alpha ($\alpha$) to the second end 28. It should be noted that the appendages 30 and 32 can be aligned at various points along the length of the baffle 16. When only one set of appendages 30 and 32 are present, it may be advantageous to position them along the central transverse axis X—X so as to make the absorbent article 76 aesthetically pleasing in appearance.

A second difference exhibited in FIG. 9 is that the first appendage 30 has an attachment member 78 secured to it just like the attachment member 40 is secured to the second appendage 32. The attachment member 78 can be a magnet. In this embodiment, since both of the appendages 30 and 32 contain a magnet, 78 and 40 respectively, it does not matter which appendage, 30 or 32, is folded first around the undergarment. The magnets 38, 40 and 78 should be designed such that when each magnet is superposed over one another, a magnetic force will be present which will attract each of the magnets to one another.

Optionally, in this embodiment, the first magnet 38 could be eliminated because the second magnet 40 and the third magnet 78 have sufficient strength to hold the absorbent article 76 to an undergarment.

PROCESS

In manufacturing any of the above-identified absorbent articles 10, 46, 66 and 76, it is possible to place a non-magnetized metal or ceramic material, which is capable of being magnetized, into the article in the desired location. After the absorbent article has been fully constructed, the article can be run through an apparatus which will magnetize the magnetic susceptible material. In this case, it is possible to magnetize the attachment members 38, 40, 52, 54 and 78, so that they will be attracted to one another. Once the article has been used and disposed of, it is possible to recover the magnetic material and run them through a machine which will demagnetize them. The metal can then be recycled and reused.

The method of attaching the absorbent article to the crotch portion of an undergarment includes the steps of positioning the absorbent article on the undergarment with said baffle contacting the interior surface of the undergarment. The first and second appendages are then folded around the crotch portion of the undergarment such that the first appendage overlays the first magnet and the second appendage overlays the first appendage. In this position, the second magnet is vertically aligned with, and magnetically attracted to the first magnet.

When two pairs of appendages are present, the first and second members of each pair are folded around the crotch portion of the undergarment such that each of the first pair of appendages overlays one of the first magnets and each of the second pair of appendages overlays one of the first appendages. In this position, each of the second magnets is vertically aligned with and magnetically attracted to one of the first magnets.

While the invention has been described in conjunction with several specific embodiments, it is to be understood that many alternatives, modifications and variations will be apparent to those skilled in the art in light of the foregoing description. Accordingly, this invention is intended to embrace all such alternatives, modifications and variations which fall within the spirit and scope of the appended claims.

I claim:

1. A method of attaching an absorbent article to a crotch portion of an undergarment, said undergarment having an interior surface and an exterior surface, said article having an absorbent, a baffle secured to said absorbent, said baffle having first and second longitudinal side edges, a first end, and first and second appendages extending laterally outward from said first and second longitudinal side edges, respectively, each of said first and second appendages positioned adjacent to said first end and aligned at an angle relative to said longitudinal side edges and having a sufficient length to be folded inward and overlap one another, and a first magnet secured to said baffle and a second magnet secured to said second appendage, said method comprising the steps of:

a) positioning said absorbent article on said undergarment with said baffle contacting said interior surface; and b) folding said first and second appendages around said crotch portion of said undergarment such that said first appendage overlays said first magnet and said second appendage overlays said first appendage, and said second magnet is vertically aligned with and magnetically attracted to said first magnet.

2. A method of attaching an absorbent article to a crotch portion of an undergarment, said undergarment having an interior surface and an exterior surface, said article having an absorbent, a baffle secured to said absorbent, said baffle having first and second longitudinal side edges, a first end, and first and second appendages extending laterally outward from said first and second longitudinal side edges, respectively, each of said first and second appendages positioned adjacent to said first end and aligned at an angle relative to said longitudinal side edges and having a sufficient length to be folded inward and overlap one another, and a first magnet secured between said absorbent and said baffle and a second magnet secured to said second appendage, said method comprising the steps of:

a) positioning said absorbent article on said undergarment with said baffle contacting said interior surface; and b) folding said first and second appendages around said crotch portion of said undergarment such that said first appendage overlays said first magnet and said second appendage overlays said first appendage, and said second magnet is vertically aligned with and magnetically attracted to said first magnet.

\* \* \* \* \*